(12) United States Patent
Golding

(10) Patent No.: US 9,087,756 B2
(45) Date of Patent: Jul. 21, 2015

(54) IMAGE SENSOR READOUT METHOD AND APPARATUS

(71) Applicant: STMicroelectronics (R&D) Ltd., Buckinghamshire (GB)

(72) Inventor: Robert Golding, Edinburgh (GB)

(73) Assignee: STMicroelectronics (Research & Development) Limited, Marlow, Buckinghamshire (GB)

( * ) Notice: Subject to any disclaimer, the term of this patent is extended or adjusted under 35 U.S.C. 154(b) by 476 days.

(21) Appl. No.: 13/710,198

(22) Filed: Dec. 10, 2012

(65) Prior Publication Data

US 2013/0155282 A1    Jun. 20, 2013

(30) Foreign Application Priority Data

Dec. 15, 2011 (GB) .................................. 1121575.3

(51) Int. Cl.
| | |
|---|---|
| H04N 5/76 | (2006.01) |
| H04N 9/64 | (2006.01) |
| H04N 5/335 | (2011.01) |
| H01L 27/146 | (2006.01) |
| H04N 5/355 | (2011.01) |
| H04N 5/378 | (2011.01) |
| G01N 21/64 | (2006.01) |

(52) U.S. Cl.
CPC .......... *H01L 27/14609* (2013.01); *H04N 5/335* (2013.01); *H04N 5/35572* (2013.01); *H04N 5/378* (2013.01); *G01N 21/645* (2013.01)

(58) Field of Classification Search
CPC ... H04N 5/378; H04N 5/35572; H04N 5/335; G01N 21/645; G01N 21/6452; G01N 61/6454; H01L 27/14609; G01J 3/2803; G01J 3/2823
USPC ........................................ 348/243, 297, 231.5
See application file for complete search history.

(56) References Cited

U.S. PATENT DOCUMENTS

| | | | |
|---|---|---|---|
| 6,809,666 B1 * | 10/2004 | Ewedemi et al. ................ 341/97 |
| 6,963,369 B1 * | 11/2005 | Olding ............................ 348/241 |
| 6,975,355 B1 * | 12/2005 | Yang et al. ..................... 348/308 |
| 7,362,365 B1 | 4/2008 | Reyneri et al. |
| 7,397,505 B2 * | 7/2008 | Brehmer et al. ............... 348/243 |
| 2001/0009440 A1 * | 7/2001 | Yang et al. ..................... 348/294 |
| 2001/0040632 A1 * | 11/2001 | Yang et al. ..................... 348/294 |

(Continued)

OTHER PUBLICATIONS

Great Britain Search Report dated Apr. 13, 2012 from corresponding Great Britain Application No. 1121575.3.

*Primary Examiner* — John Villecco
(74) *Attorney, Agent, or Firm* — Gardere Wynne Sewell LLP

(57) ABSTRACT

A pixel readout circuit including at least first, second and third memory locations. During an integration period of a pixel, the pixel readout circuit repeatedly samples the pixel output level during the integration period, stores the first sample in the first memory location, and stores each subsequent sample in memory locations other than the first memory location. Each sample is stored with a time corresponding to when that sample was taken, such that at any one time subsequent to the first three samples having been stored, at least the first sample and the two most recent samples are stored. Also disclosed is a corresponding method of reading out of a pixel output over an undefined integration period.

20 Claims, 3 Drawing Sheets

(56) References Cited

U.S. PATENT DOCUMENTS

| | | | |
|---|---|---|---|
| 2002/0140834 A1* | 10/2002 | Olding et al. | 348/294 |
| 2003/0076432 A1* | 4/2003 | Luo et al. | 348/308 |
| 2003/0095189 A1* | 5/2003 | Liu et al. | 348/208.4 |
| 2003/0098919 A1* | 5/2003 | Liu et al. | 348/297 |
| 2004/0234417 A1* | 11/2004 | Schienle et al. | 422/82.08 |
| 2006/0176401 A1* | 8/2006 | Turchetta | 348/571 |
| 2008/0055440 A1* | 3/2008 | Pertsel et al. | 348/297 |
| 2008/0316347 A1* | 12/2008 | Gamal et al. | 348/296 |

* cited by examiner

IMAGE SENSOR READOUT METHOD AND APPARATUS

CROSS REFERENCE TO RELATED APPLICATIONS

This application claims the priority benefit of Great Britain patent application number 1121575.3, filed on Dec. 15, 2011, which is hereby incorporated by reference to the maximum extent allowable by law.

BACKGROUND

1. Technical Field

The present disclosure relates to the field of digital image sensors, and in particular to the field of high dynamic range methods for such sensors.

2. Discussion of the Related Art

Digital image sensing based upon solid state technology is well known, the two most common types of image sensors currently being charge coupled devices (CCDs) and complementary metal oxide semiconductor (CMOS) image sensors. Digital image sensors are incorporated within a wide variety of devices throughout the consumer, industrial and defence sectors among others.

An image sensor is a device comprising one or more radiation sensitive elements having an electrical property that changes when radiation is incident upon them, together with circuitry for converting the changed electrical property into a signal. As an example, an image sensor may comprise a photodetector that generates a charge when radiation is incident upon it. The photodetector may be designed to be sensitive to electromagnetic radiation in the range of (human) visible wavelengths, or other neighbouring wavelength ranges, such as infra red or ultra violet for example. Circuitry is provided that collects and carries the charge from the radiation sensitive element for conversion to a value representing the intensity of incident radiation.

Typically, more than one radiation sensitive element will be provided in an array. The term pixel is used as a shorthand for picture element. In the context of a digital image sensor, a pixel refers to that portion of the image sensor that contributes one value representative of the radiation intensity at that point on the array. These pixel values are combined to reproduce a scene that is to be imaged by the sensor. A plurality of pixel values can be referred to collectively as image data. Pixels are usually formed on and/or within a semiconductor substrate. In fact, the radiation sensitive element comprises only a part of the pixel, and only part of the pixel's surface area (the proportion of the pixel area that the radiation sensitive element takes up is known as the fill factor). Other parts of the pixel are taken up by metalization such as transistor gates and so on. Other image sensor components, such as readout electronics, analog to digital conversion circuitry and so on may be provided at least partially as part of each pixel, depending on the pixel architecture.

One of the most important characteristics of any image sensor is its dynamic range, that is, the ratio between the minimum and the maximum signal that can be successfully reproduced by the image sensor. There are various fields in which a high or very high dynamic range is required.

One such device where a wide dynamic range is required is a biosensor. In a biosensor, each pixel is exposed to a substance suspected of containing target diseases/chemicals/proteins etc. which is then treated with a chemical that reacts specifically with the target. This reaction produces light which is then detected by the biosensor. Different targets and their corresponding chemicals can be put on different pixels on the biosensor array, such that the system can analyze a wide range of samples at once. However, it is often the situation that each pixel will receive vastly different light levels. Some pixels saturate in fractions of seconds, while others may take up to 30 seconds to saturate.

It would be desirable, therefore, to provide readout circuitry able to analyze all these signals, therefore greatly increasing the pixel array's dynamic range.

SUMMARY

In a first aspect there is provided a pixel readout circuit comprising at least first, second and third memory locations wherein, during an integration period of a pixel, said pixel readout circuit is operable to repeatedly sample the pixel output level during the integration period, to store the first sample in said first memory location, and to store each subsequent sample in memory locations other than said first memory location, each sample being stored with a time corresponding to when that sample was taken, such that at any one time subsequent to the first three samples having been stored, at least the first sample and the two most recent samples are stored.

Said memory locations may comprise separate SRAMs. Three SRAMs may be provided per readout circuit. Each sample subsequent to the first and its corresponding time may be alternately stored in said second and third memory locations.

Said pixel readout circuit may be operable to sample the pixel output level at set intervals.

The pixel readout circuit may be operable to cease sampling of the pixel output level when the pixel output level reaches a predetermined threshold, which may be determined relative to the pixel saturation level. The pixel readout circuit may be operable to perform correlated sampling of said pixel output, using the contents of said first memory location and the contents of the memory location in which the penultimate sample taken is stored.

The pixel readout circuit may comprise a global counter for calculating said times corresponding to when each sample was taken, relative to the beginning of the pixel integration period.

The pixel readout circuit may comprise a ramp generator that may be operable to begin ramping at the beginning of each sample.

Said pixel readout circuit is further operable to store the time taken to pixel saturation.

In a further aspect there is provided a digital image sensor comprising an array of pixels, wherein each pixel has a corresponding pixel readout circuit according to the first aspect of the invention. Also provided is a biosensor comprising such a digital image sensor.

In a yet further aspect there may be provided of reading out of a pixel output over an undefined integration period, comprising the steps of: repeatedly sampling the pixel output level during said integration period; storing the first sample in a first memory location along with a time corresponding to when the first sample was taken; storing each subsequent sample in memory locations other than said first memory location along with a time corresponding to when that sample was taken, such that at any one time at least the first sample and the two most recent samples are stored.

Said subsequent samples may be taken and stored until such time as the pixel output level reaches a predetermined threshold. Said predetermined threshold may be determined relative to the pixel saturation level. Once said sampling has ceased, the contents of said first memory location and the contents of the memory location in which the penultimate sample taken is stored may be used in correlated sampling of the pixel output.

The method may be performed for multiple pixels over different integration periods.

Said method may further include storing the time taken to saturation for the/each pixel.

Said method may further include sampling the pixel output level at set intervals.

Said method may comprise a method of performing correlated double sampling. If so, each subsequent sample, and its corresponding time, may be alternately stored in second and third memory locations.

BRIEF DESCRIPTION OF THE DRAWINGS

Aspects of the disclosure will now be described, by way of example only, with reference to the accompanying drawings in which.

DETAILED DESCRIPTION

Biosensors are analytical tools that detect the presence of a chemical or biochemical species in a complex mixture by combining the molecular recognition properties of biological macromolecules (e.g., enzymes, antibodies, DNA or even whole cells) with signal transduction mechanisms (e.g., optical or electrochemical) that couple ligand bindings with readily detectable physical changes.

The optical signal transduction mechanisms employed by biosensors are based on luminescence spectroscopy, absorption spectroscopy (ultraviolet (UV) to deep infrared (IR)), Raman or fluorescence spectroscopy. Fluorescence spectroscopy will be described in detail below, purely by way of example. However the readout circuitry and photodetector arrangements disclosed herein are equally applicable to any other type of optical biosensor such as those mentioned above, as well as to other photodetector/imaging applications in general.

To increase analytical throughput, an analytical process should be capable of simultaneously detecting a number of different species. Biosensor arrays achieve this by assembling a large number of different biological macromolecules (each of which contains a recognition site for a given biological species, with such species being known henceforth as an analyte) into densely packed arrays of unique sensor elements.

Biosensor arrays have three main operational mechanisms, namely labeled analyte pooling (used in DNA and RNA hybridization assays), sandwich assays (used for antibody recognition) and direct assays.

Figure 1:
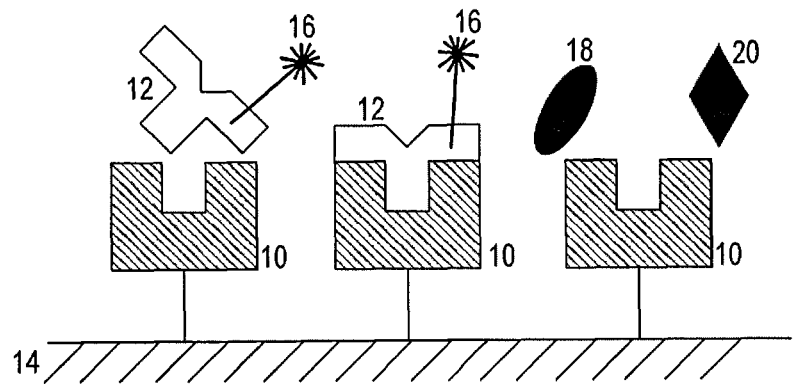
FIG. 1 is a block diagram of one of the operating mechanisms of a fluorescence biosensor according to the prior art.

Referring to FIG. 1, during labeled analyte pooling a biological macromolecule 10 specific for an analyte 12 is immobilized on a solid support 14. A sample (containing an analyte 12) is mixed with a solution of a fluorescent label 16 that binds to the analyte 12 therein. The sample is then introduced to the biosensor array and the analyte 12 therein is bound to the biological macromolecule 10 specific therefore. Other species 18, 20 in the sample that are not of analytical interest (and for which there are no biological macromolecules immobilized on the solid support 14) remain in free solution.

The support 14 is then washed with a cleaning solution (not shown) and any unbound species in the sample are flushed therefrom, leaving the fluorescently labeled analyte 12 bound to the support 14. The fluorescently labeled analyte 12 fluoresces when exposed to radiation (e.g., from an IR laser) and the resulting fluorescent pattern of the biosensor array acts as a biochemical fingerprint that can be readily imaged.

Figure 2:
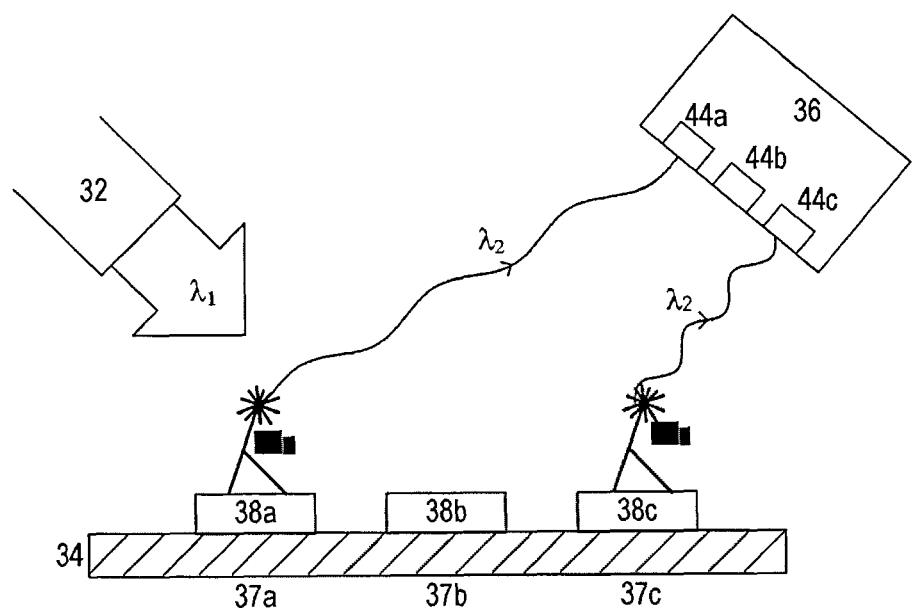
FIG. 2 is a block diagram of a generic conventional fluorescence biosensor according to the prior art.

Referring to FIG. 2, a fluorescence biosensor 30 typically comprises a stimulating light source 32, a substrate 34 and a photodetector 36. The substrate 34 comprises a plurality of sensor elements 37a, 37b and 37c each of which comprises an immobilized biological macromolecule 38a, 38b and 38c specific for a particular analyte of interest. While FIG. 2 shows the photodetector 36 disposed remotely from the substrate 34, nonetheless, it will be appreciated that this arrangement is not essential and the substrate 34 could alternatively be configured to house both the photodetector 36 and the sensor elements 37a, 37b and 37c.

Using, for example, the above-described labeled analyte pooling scheme, analytes 40a and 40c in a sample have fluorescent labels bound thereto. When the sample (not shown) is introduced to the substrate 34, the labeled analytes 40a and 40c bind to the appropriate macromolecule 38a and 38c. However, if an analyte that binds to a particular macromolecule 38b is not present in the sample, the corresponding sensor element 37b remains free of labeling.

The light source 32 emits light 42 of wavelength $\mu_1$, which is a stimulating wavelength for the fluorescent labels (bound to the analytes 40a and 40c). The light source 32 is positioned so that the light 42 it emits falls upon the sensor elements 37a, 37b and 37c (and any fluorescently labeled analytes bound thereto). It will be appreciated that there may be some additional optical elements (e.g., lens, lightguide, etc.) disposed between the light source 32 and the sensor elements 37a, 37b and 37c. It will also be appreciated that the light source 32 may alternatively scan the array of sensor elements 37a, 37b and 37c. The light 42 stimulates the fluorescent labels bound to the analytes 40a and 40c to emit radiation of wavelength $\lambda_2$ ($\lambda_1 < \lambda_2$)

The photodetector 36 comprises a plurality of pixels 44a, 44b and 44c, each of which is positioned to detect the radiation emitted from a given sensor element 37a, 37b and 37c. As before, it will be appreciated that there may be some additional optical elements (e.g. lens, a light guide, etc.) disposed between the sensor elements 37a, 37b and 37c and the photodetector 36. It will also be appreciated that the photodetector 36 may alternatively scan the array of sensor elements 37a, 37b and 37c.

Radiation may be emitted from sensor elements 37a, 37b and 37c at vastly differing rates such that, over a given time, different pixels 44a, 44b and 44c may receive vastly differing light levels. Consequently, some pixels saturate in fractions of seconds, while others may take up to 30 seconds to saturate. Therefore the individual pixels of the pixel array may be exposed with varying integration times. This provides a challenge for the readout circuitry for the pixel array.

It is proposed to provide a readout circuit which samples the voltage level of a pixel output repeatedly at set intervals during the pixel integration time.

Figure 3:
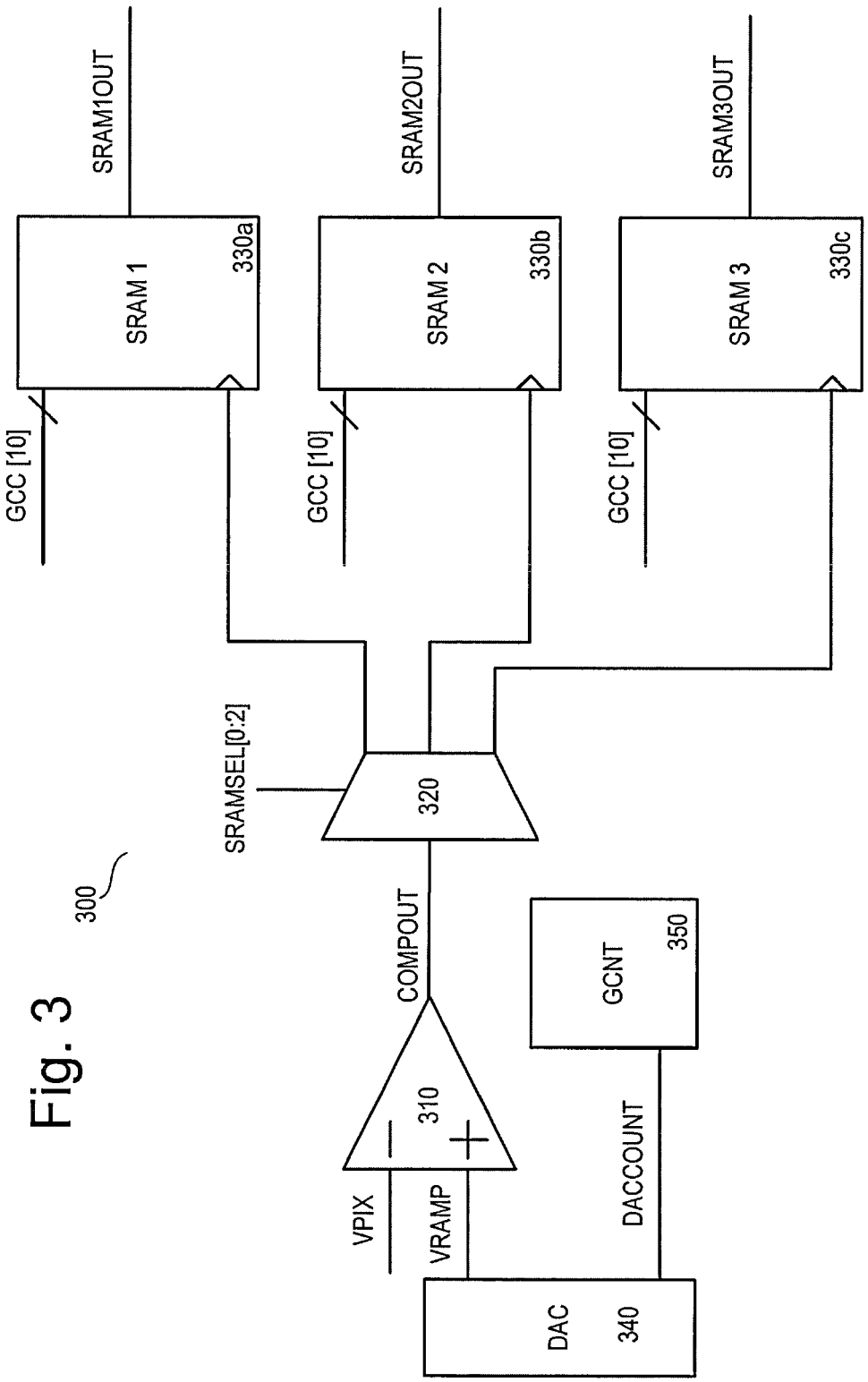
FIG. 3 is a pixel readout circuit according to an embodiment.

FIG. 3 shows a readout circuit 300 according to an embodiment. It is proposed that one such readout circuit 300 is provided for each pixel of the pixel array. The readout circuit 300 comprises a comparator 310, the output of which is connected to three (in this example) static random access memories SRAMs 330a, 330b, 330c via a multiplexer 320. The comparator 320 receives the pixel output signal VPIX and a ramp signal VRAMP generated by a digital to analogue converter (DAC) 340. The DAC also provides a global counter output signal DACCOUNT which is used to increment a global counter 350. This is separate from the analogue to digital converter (ADC) and its associated counter (not shown), which operates in a known way to provide a digital equivalent to the signal VPIX each time that it is sampled.

This circuit is operable to compare the signal VRAMP from the DAC 340 to the pixel output signal VPIX. When the signals VPIX and VRAMP cross, the output COMPOUT of comparator 310 will flip and a digital representation of pixel output VPIX (as converted by an ADC, not shown) will be stored on one of the SRAMs 330a, 330b, 330c. The appropriate SRAM 330a, 330b, 330c is selected using the input SRAMSEL of multiplexer 320. The values stored in the SRAMs 330a, 330b, 330c can be read out as SRAM1OUT, SRAM2OUT and SRAM3OUT when required. Each SRAM 330a, 330b, 330c also receives counter signal GCC (Gray Code Count).

Figure 4:
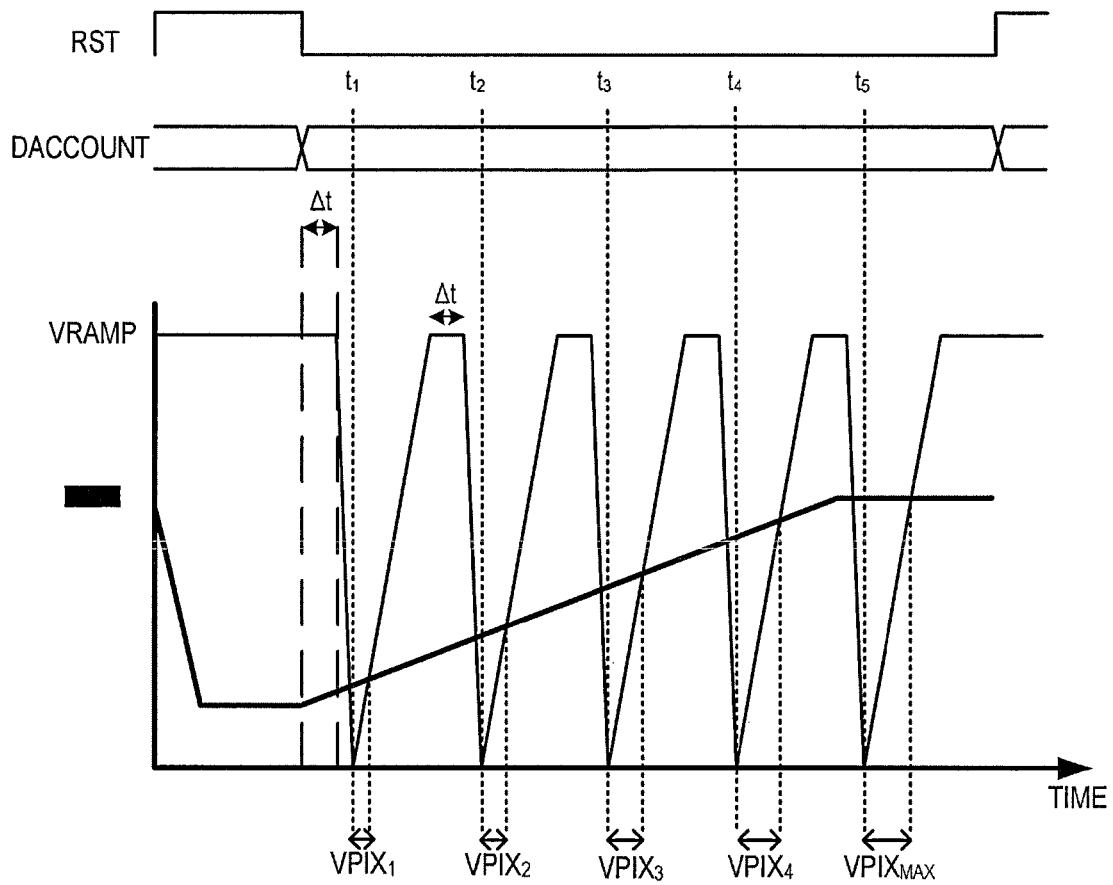
FIG. 4 is a timing diagram showing a operation embodiment of the pixel readout circuit of FIG. 3.
Figure 5:
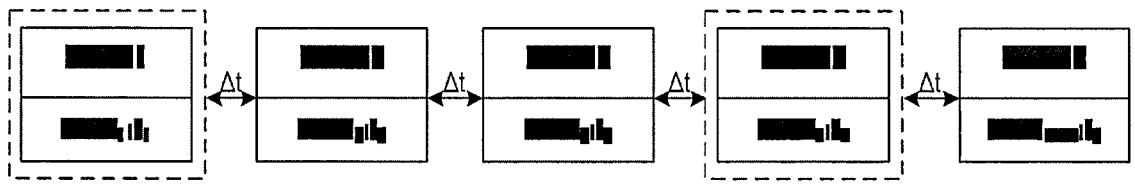
FIG. 5 is a diagram illustrating how the memory contents of the of the pixel readout circuit of FIG. 3 change over time.

FIG. 4 is a timing diagram showing the Pixel reset signal RST, timer signal DACCOUNT, pixel output signal VPIX and ramp signal VRAMP over time during an operational embodiment of the readout circuit of FIG. 3. FIG. 5 illustrates how the contents of the SRAMs 330a, 330b, 330c change over time.

In this operational embodiment, the pixel output signal VPIX is sampled immediately after pixel reset. A digital representation of pixel output $VPIX_1$ after a configurable time $\Delta t$ is stored in one of the SRAMs, for example SRAM1 330a. Also stored is the time $t_1$, as counted by the DAC global counter (signal DACCOUNT), at which this initial reading was taken. These values remain stored during the entire integration period of the pixel, and can be used as the "black level" or base reading in a correlated double sampling (CDS) calculation (or correlated multiple sampling calculation where there are more than three SRAMs), in combination with the final stored pixel output level.

Subsequent to this initial value being taken, the pixel output level VPIX is repeatedly sampled at set sampling points separated by time $\Delta t$, during the pixel integration period. The (digital) pixel output level VPIX sampled at each time is stored in an alternate one of SRAM2 330b and SRAM3 330c, overwriting any prior stored value in the process. Also stored with each pixel output value VPIX is the corresponding time that the level was sampled, as counted by the DAC's global counter DACCOUNT. This time is used to place each of these pixel output values VPIX at specific times along the decay time of the VPIX signal. This allows CDS sampling as voltages with specific sampling times along the decay line can be taken.

In the specific example shown in FIGS. 4 and 5, SRAM2 330b stores the pixel output value $VPIX_2$ and the time it was sampled $t_2$. Subsequently, SRAM3 330c stores the pixel output value $VPIX_3$ and time $t_3$, after which SRAM2 330b stores the pixel output value $VPIX_4$ and time $t_4$ (overwriting $VPIX_2$ and $t_2$ in the process). This is continued until the pixel is saturated ($VPIX=VPIX_{MAX}$), or pixel output signal VPIX reaches another predetermined threshold (for example $VPIX=0.9VPIX_{MAX}$). When it is determined that the last stored value is the maximum saturated value of the pixel output VPIX, sampling is immediately stopped, and the penultimate sample value and corresponding time is used as the final pixel reading in the CDS calculation, in combination with the black level values stored initially. In the specific example shown in FIG. 5, the values used are those ringed with a dashed line, that is $VPIX_1$ and $t_1$ stored on SRAM1 330a and $VPIX_4$ and $t_4$ stored on SRAM2 330b. The time to saturation $t_5$ can also be stored, providing more information on the specific pixel.

A pixel array with varying integration times for each pixel can utilise this circuitry to read out any pixel, regardless of the array integration time or pixel voltage gradient using CDS under a single ramp ADC. Such circuitry can operate on systems without auto exposure control, and allows the pixel voltage to ramp at a wide range of gradients, be it as a result of a charge integrator or any other slope dependent readout.

Various improvements and modifications may be made to the above without departing from the scope of the disclosure. For example, more than three SRAMs may be used, particularly where correlated multiple sampling is desirable. And other types of memory or storage could be used in place of SRAM. Also, while the readout circuit is described in relation to use with a biosensor, it may be used with any pixel array, specifically where a large dynamic range is desirable. This may include imaging devices such as inter alia a camera.

Such alterations, modifications, and improvements are intended to be within the spirit and scope of the invention. Accordingly, the foregoing description is by way of example only and is not intended as limiting. The invention is limited only as defined in the following claims and the equivalents thereto.

What is claimed is:

1. A pixel readout circuit comprising at least first, second and third memory locations wherein, during an integration period of a pixel, said pixel readout circuit is operable to repeatedly sample the pixel output level during the integration period, to store the first sample in said first memory location, and to store each subsequent sample in memory locations other than said first memory location, each sample being stored with a time corresponding to when that sample was taken, such that at any one time subsequent to the first three samples having been stored, at least the first sample and the two most recent samples are stored.

2. A pixel readout circuit as claimed in claim 1 wherein said memory locations comprise separate SRAMs.

3. A pixel readout circuit as claimed in claim 1, wherein each sample subsequent to the first and its corresponding time is alternately stored in said second and third memory locations.

4. A pixel readout circuit as claimed in claim 1, wherein said pixel readout circuit is operable to sample the pixel output level at set intervals.

5. A pixel readout circuit as claimed in claim 1, operable to cease sampling of the pixel output level when the pixel output level reaches a predetermined threshold.

6. A pixel readout circuit as claimed in claim 5 operable such that said predetermined threshold is determined relative to the pixel saturation level.

7. A pixel readout circuit as claimed in claim 5 operable, once said sampling has ceased, to perform correlated sampling of said pixel output using the contents of said first memory location and the contents of the memory location in which the penultimate sample taken is stored.

8. A pixel readout circuit as claimed in claim 1, wherein said pixel readout circuit comprises a global counter operable to calculate said times corresponding to when each sample was taken, relative to the beginning of the pixel integration period.

9. A pixel readout circuit as claimed in claim 1, wherein said pixel readout circuit comprises a ramp generator that is operable to begin ramping at the beginning of each sample.

10. A pixel readout circuit as claimed in claim 1, wherein said pixel readout circuit is further operable to store the time taken to pixel saturation.

11. A digital image sensor comprising an array of pixels, wherein each pixel has a corresponding pixel readout circuit according to claim 1.

12. A biosensor comprising a digital image sensor according to claim 9.

13. A method of reading out of a pixel output over an undefined integration period, comprising the steps of:
  repeatedly sampling the pixel output level during said integration period;
  storing the first sample in a first memory location along with a time corresponding to when the first sample was taken;
  storing each subsequent sample in memory locations other than said first memory location along with a time corresponding to when that sample was taken, such that at any one time at least the first sample and the two most recent samples are stored.

14. The method of claim 13 wherein said subsequent samples are taken and stored until such time as the pixel output level reaches a predetermined threshold.

15. The method of claim 14 wherein said predetermined threshold is determined relative to the pixel saturation level.

16. The method of claim 14 further comprising, once said sampling has ceased, using the contents of said first memory location and the contents of the memory location in which the penultimate sample taken is stored in correlated sampling of the pixel output.

17. The method of claim 13, being performed for multiple pixels over different integration periods.

18. The method of claim 13, wherein said method further includes storing the time taken to saturation for the/each pixel.

19. The method of claim 13, further including sampling the pixel output level at set intervals.

20. The method of claim 13, wherein each subsequent sample, and its corresponding time, is alternately stored in second and third memory locations, said method comprising a method of performing correlated double sampling.

* * * * *